US008448345B2

(12) United States Patent
Vidal et al.

(10) Patent No.: US 8,448,345 B2
(45) Date of Patent: May 28, 2013

(54) HAIR MEASURING ASSEMBLY AND SINGLE USE CARTRIDGE

(75) Inventors: Michael Vidal, Miami, FL (US); Ravi Sawhney, Thousand Oaks, CA (US); Kurt Botsai, Thousand Oaks, CA (US); Lance Hussey, Thousand Oaks, CA (US); John Vernon, Thousand Oaks, CA (US); Leah Thomas, Thousand Oaks, CA (US)

(73) Assignee: Iberius LLC, Miami, FL (US)

( * ) Notice: Subject to any disclaimer, the term of this patent is extended or adjusted under 35 U.S.C. 154(b) by 341 days.

(21) Appl. No.: 12/661,768

(22) Filed: Mar. 23, 2010

(65) Prior Publication Data

US 2010/0256519 A1    Oct. 7, 2010

Related U.S. Application Data

(60) Provisional application No. 61/210,860, filed on Mar. 23, 2009, provisional application No. 61/339,727, filed on Mar. 8, 2010.

(51) Int. Cl.
*A61B 1/00*    (2006.01)

(52) U.S. Cl.
USPC ............................................. 33/512; 600/587

(58) Field of Classification Search
USPC .............................. 33/511, 512; 600/562–572
See application file for complete search history.

(56) References Cited

U.S. PATENT DOCUMENTS

| | | | | |
|---|---|---|---|---|
| 5,287,631 A * | 2/1994 | Stade | ............................... | 33/823 |
| 5,345,692 A * | 9/1994 | Babitchenko | ................... | 33/828 |
| 6,014,886 A * | 1/2000 | Anderson et al. | .............. | 73/1.81 |
| 6,993,851 B2 * | 2/2006 | Cohen | .............................. | 33/512 |
| 7,076,886 B2 | 7/2006 | John et al. | | |
| 7,131,208 B2 * | 11/2006 | Cohen | .............................. | 33/512 |
| RE41,046 E * | 12/2009 | Cohen | .............................. | 33/512 |
| D649,892 S * | 12/2011 | Vidal et al. | ...................... | D10/70 |
| 2005/0229418 A1 * | 10/2005 | Cohen | .............................. | 33/512 |
| 2006/0005409 A1 * | 1/2006 | Cohen | .............................. | 33/512 |
| 2006/0259070 A1 | 11/2006 | Livneh | | |
| 2007/0106297 A1 * | 5/2007 | Dumbauld et al. | ............. | 606/51 |
| 2009/0012556 A1 * | 1/2009 | Boudreaux et al. | ........... | 606/206 |
| 2010/0004677 A1 * | 1/2010 | Brostoff et al. | ............... | 606/205 |

FOREIGN PATENT DOCUMENTS

| | | |
|---|---|---|
| WO | WO 2005/102164 A1 | 11/2005 |
| WO | WO 2010/110858 A1 | 9/2010 |

* cited by examiner

*Primary Examiner* — Sean P Dougherty
*Assistant Examiner* — Michael C Stout
(74) *Attorney, Agent, or Firm* — Malloy & Malloy, P.L.

(57) ABSTRACT

A hair measuring assembly capable of being operated by a single hand of a user and including a collection assembly, including a hair retaining and measuring portion movably mounted on a body and selectively disposable between a collecting position and a retaining and measuring position. The single handed manipulation of a hand grip, concurrently disposes a plurality of two grip segments into either an open or a closed orientation, thereby forcing the hair retaining and measuring portion between the collecting and hair retaining and measuring positions. A "single use" cartridge for carrying out the collection, retention and measurement of hair and also hair breakage is presented. The "single use" cartridge includes suitable structure for mounting and operable attachment to the hair measuring assembly by a person, without regard to whether he or she is left-handed or right-handed.

26 Claims, 10 Drawing Sheets

HAIR MEASURING ASSEMBLY AND SINGLE USE CARTRIDGE

CLAIM OF PRIORITY

The present application is based on and a claim to priority is made under 35 U.S.C. Section 119(e) to provisional patent application Ser. No. 61/210,860 filed on Mar. 23, 2009, and provisional patent application Ser. No. 61/339,727 filed on Mar. 8, 2010, both of which are herein incorporated by reference in their entirety.

BACKGROUND OF THE INVENTION

1. Field of the Invention

The present invention is directed to a hair measuring assembly capable of being operated by a single hand of a user through manipulation of a hand grip that is movably connected to the body of the device. The hand grip of the assembly preferably includes two grip segments, such that a concurrent, pivotal and lateral displacement of the grip segments position a hair retaining and measuring portion of a hair collection assembly between a collecting position for gathering the hair to be measured, and a retaining and measuring position, wherein the collected hair is at least minimally compressed and measured. The free hand of the user, i.e., that which is not associated with the hand grip, may thereby be used to hold and/or properly position the hair to be measured for efficient collection thereof, by and within the hair retaining and measuring portion. The present invention additionally comprises a "single use" cartridge for carrying out the collection, retention and measurement of hair so as to evaluate the existence of hair loss, and ideally also, hair breakage, and further, includes suitable structure for mounting an operable attachment to the body of the hair measuring assembly by a person, without regard to whether he or she is left-handed or right-handed.

2. Description of the Related Art

Hair loss, which is also medically termed "alopecia," describes the loss of hair from the head or body, and for some people can result in complete baldness or more commonly, in many men there can be a partial, but fairly substantial, loss of hair that is often referred to as "male patterned baldness." Aside from genetic issues, it has long been recognized that hair loss may also occur from some medical conditions which affect an individual's health, as well as from some psychological conditions, including in some cases, it is said, stress, anxiety, etc. In addition, physical treatment of the hair such as hair styling, coloring, hair straightening and other processing and/or compositions applied to the hair may also result in mild or severe hair loss. Regardless, hair loss is a problem which concerns both men and women, and absent the existence of medical and other conditions of the type set forth above, is most often experienced later in life. In other words, the normal aging process frequently involves individuals losing scalp hair at a gradual but recognizable rate.

Hair is believed to grow in cycles or phases comprising a "growing phase," an "in-between phase," and a resting or "hair loss phase." It is thought that many factors determine whether hair loss is permanent or cyclical in nature. In either case, the rate of hair loss can be determined by accurately measuring hair density or quantity. The permanent loss of hair often occurs at or along a specific location on the scalp. By way of example, hair loss in men may typically follow a pattern resulting in "male patterned baldness". In contrast, hair loss in women may follow a significantly different pattern, wherein the loss of hair occurs at different rates and for different periods of time. Moreover, because many women color or otherwise chemically treat their hair, which can weaken the structure of the hair shaft, they often experience some breakage of the hair strands at various lengths thereof. Such "hair breakage" can mean that some women are unable to grow their hair long or to what they might consider a more desirable length.

Scalp hair normally lasts anywhere from two to seven years. However, as set forth above, the growing phase or cycle may be interrupted by certain medications, diseases or physical mistreatment of the hair. The hair-loss phase typically lasts a few months and is slowed in individuals having healthy hair and scalp by the growing of new hair. As a result, a "shedding" of the hair occurs, to the extent that it is normal to lose 50 or more hairs a day. Excessive shedding of the hair may occur for a brief period after an event such a childbearing, fever, surgery, weight loss or exposure of the individual to certain medications.

The ability to diagnose abnormal hair loss in its early stages is often difficult and may be more evident in some individuals rather than others based, at least part, on contrasting colors of the scalp and hair. More specifically, a visual contrast in the color of different portions of a person's hair, as compared to the scalp, may be a clear indication of the on-set of hair loss. By way of example only, individuals with dark hair and contrasting lighter skin color may make the visual observation of hair loss more evident, even early in the hair loss process. In contrast, individuals with blond hair and light skin may endure significant hair loss without such loss being visually evident, due to a minimal contrast between the colors of the scalp and the hair. However, in either situation, the rate and severity of hair loss cannot be ascertained without a more accurate means of measurement.

In recent years, various treatments for hair loss, as well as hair breakage, have been available to the general public. These treatments may take the form of applying conditioners and other compositions to strengthen the hair shaft, or with regard to hair loss, specific compositions and/or medications which are purported to increase hair growth or to prevent or reverse hair loss or balding. In more extreme situations, surgical procedures are available for hair loss, which are intended to move the healthy or growing hair of an individual, sometimes referred to as "plugs" of hair, from one part of the scalp to a different portion of the scalp where hair has been lost. While considering that there are various factors associated with the treatment of hair loss, as generally outlined above, many people view the overall and/or long term effectiveness of such treatment(s) to be somewhat subjective.

Without regard as to which treatments for baldness work, work well, or do not work, there is an appreciable need in the field of art relating to hair loss for a practical and effective way of determining the existence as to hair loss, and the rate at which such hair loss is occurring, regardless of the cause. As such, a hair measuring device has been developed that can accomplish a reasonably accurate measurement of hair density on various portions of the scalp, as set forth in U.S. Pat. Nos. 6,993,851 and 7,131,208 issued on Feb. 7, 2006 and Nov. 7, 2006, respectively, the latter of which having been reissued in December of 2009, and the contents of all of which are hereby incorporated by reference in their entireties.

Ideally, however, the hair measuring device described in the aforesaid patents and/or any other hair measuring device, should be capable of being constructed to have a "single use" cartridge structured to measure and/or which assist with the efficient and accurate measurement of hair, but which can be easily removed from the device after use on an individual, and replaced with a new or fresh cartridge, for use of the device subsequently on another person or if desired, on, the same person. In addition, if any such "single use" cartridge were developed, it would ideally be attachable to the hair measuring device by a user without regard to whether he/she is left handed or right handed. Moreover, if any such cartridge were developed, it would ideally offer as well the ability to measure hair breakage. Furthermore, the hair measuring device described in the aforesaid patents and/or any other hair measuring device, should ideally also be constructed so as to have a hand grip as part of or operably connected thereto and which can be operated by a single hand of a user, whether a medical doctor or other trained person, in a simple and easy manner for taking measurements, or even repeated measurements of the hair on an individual's scalp. As a result, the user of the device would have one free hand, i.e., that which is not associated with the hand grip, to use for holding and/or properly positioning the hair to be measured for efficient collection thereof, regardless of whether that user is primarily left-handed or right-handed.

SUMMARY OF THE INVENTION

This invention is intended to present a solution to these and other needs in this field of art, and as such, is directed to an improved hair measuring assembly. The hair measuring assembly of the present invention is also structured so as to be capable of operation with a single use cartridge, for reasons described more in detail herein. In addition, the hair measuring assembly of the present invention is structured so as to be capable of operation by a single hand of a user, and further, so as to accurately measure hair density growing from a substantially isolated portion of an individual's scalp, which portion has a predetermined dimension. As such, the assembly of the present invention can be used to repeatedly take measurements of the density of hair, issuing preferably from substantially the same isolated portion of the scalp, in order to determine the existence of continued hair loss or the growth of hair. The effectiveness of any treatment an individual may be undergoing can, thereby, be determined by the change in the density of the hair being measured.

Accordingly, the improved hair measuring assembly of the present invention comprises a substantially elongated body that is made from a material which is sufficiently light weight so that the assembly may be easily handled and manipulated. In addition, a collection assembly is connected to an outer or distal end of the body and includes a hair retaining and measuring portion that is movable relative to the body between a hair collecting position and a hair retaining and hair measuring position. Moreover, the hair retaining and measuring portion includes an at least partially open space or area, in which the hair to be measured may be relatively quickly and efficiently collected, retained and measured through manipulation of an activating assembly.

The activating assembly comprises a hand grip including at least one, but preferably, a plurality of two grip segments, each being pivotally connected to the body of the hair measuring assembly. Further, the grip segments are cooperatively disposed and dimensioned with one another and with the body so as to be concurrently engaged and pivotally displaced laterally towards and away from the body by a single hand of the user. Therefore, the two grip segments can be selectively disposed between a normally open orientation and a closed orientation. The normally open orientation is more specifically defined by the two grip segments being disposed laterally outward from the body and in an angular orientation relative thereto. However, even when in the outwardly, spaced apart open orientation, the two grip segments can be concurrently compressed and therefore, pivotally disposed into a closed orientation, which may be defined by a substantially longitudinal alignment with the remainder of the length of the body.

The single handed operation or manipulation of the activating assembly will serve to selectively dispose the hair retaining and measuring portion between the aforementioned collecting position, and hair retaining and hair measuring positions. Such precise and efficient disposition of the hair retaining and measuring portion, relative to the hair being measured, is facilitated, at least in part, due to the provision of a linkage assembly. More specifically, the linkage assembly includes at least a first linkage structure and a second linkage structure interacting with one another. As such, the first linkage structure pivotally connects the two grip segments of the hand grip to the second linkage structure. Cooperatively, the second linkage structure is disposed to movably interconnect the hair retaining and measuring portion to the first linkage structure and accordingly, in direct, pivotally interconnecting relation to the hand grip. Therefore, as the hand grip is selectively disposed between the open and closed orientations, the interaction of the first and second linkage structures serves to precisely dispose the hair retaining and measuring portion between the aforementioned hair collecting position and hair retaining and measuring positions.

It should be pointed out that the cooperative structural and operative features of the hand grip, the linkage assembly and the hair retaining and measuring portion allows a user to manipulate the improved hair measuring assembly of the present invention by using only a single hand. In turn, this allows the user to use the other, free hand to hold, position and/or accurately manipulate the hair being measured so as to further facilitate its placement within the measuring space of the hair retaining and measuring portion. Moreover, a single hand of the user may cause the two grip segments to be concurrently and pivotally disposed into the aforementioned closed orientation. Further, as the retaining portion is moved into the retaining and measuring positions, the hair being measured will be retained and eventually, appropriately compressed as the hair retaining and measuring portion moves inwardly, and in closer proximity to the body and/or a cooperative housing portion of the collection assembly, to be described in greater detailed hereinafter. When the hair being measured is compressed in the manner set forth above, a measuring and/or display assembly is disposed and structured to display indicia representative of the dimensional characteristics of the hair collected and retained within the hair retaining and measuring portion.

Additional structural features of the various components of the improved hair measuring assembly are present in one or more of the preferred embodiments thereof. More specifically, the collection assembly including the aforementioned hair retaining and measuring portion also includes a housing or covering. In at least one embodiment, the housing is cooperatively disposed and structured with the hair retaining and measuring portion to accomplish an appropriate compression of the hair being measured as the hair retaining and measuring portion passes from the collecting position through a hair retaining position and into a hair retaining and measuring position.

Yet an additional feature of the collection assembly includes a "single use" cartridge or embodiment that allows for the removable connection of the collection assembly from the body, including both the hair retaining and measuring portion and the cover or housing associated therewith. As such, the collection assembly specifically, but not exclusively, including the hair retaining and measuring portion, may be removably connected to the aforementioned second linkage structure so as to be discarded and replaced with another "single use" cartridge in order to assure an individual having bundles of his or her hair measured, that careful hygiene is being maintained. Additionally, this "single use" cartridge or embodiment includes suitable structure for mounting and operable attachment to the improved hair measuring assembly by a person, without regard to whether he or she is left-handed or right-handed. Further, the "single use" application of a hair retaining and measuring portion may be assured through the provision of a locking member or assembly associated therewith. Such a locking member may be cooperatively disposed relative to an interior of the housing or portions of the body to prevent movement of the hair retaining and measuring portion back into a hair collecting position, once and/or after the hair retaining and measuring portion is moved into the hair retaining position and hair measuring position for compression and measurement of the collected hair.

Therefore, in the various preferred embodiments of the improved hair measuring assembly of the present invention, a user is permitted, without assistance, to accurately and efficiently measure hair density from a specific portion of an individual's scalp through the manipulation and operation of the assembly using only a single hand. As such, the activation assembly, including the hand grip, may be disposed between the aforementioned open orientation and closed orientation, thereby quickly and accurately disposing the hair retaining and measuring portion between the hair collecting position, the hair retaining position, and then the hair retaining and measuring position. As also set forth above, the hair retaining and measuring position may be further defined by a position of the hair retaining and measuring portion in sufficiently close proximity to the body and/or cooperative components of the collection assembly to facilitate an appropriate compression of the hair being measured in order to accomplish an accurate measurement thereof.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
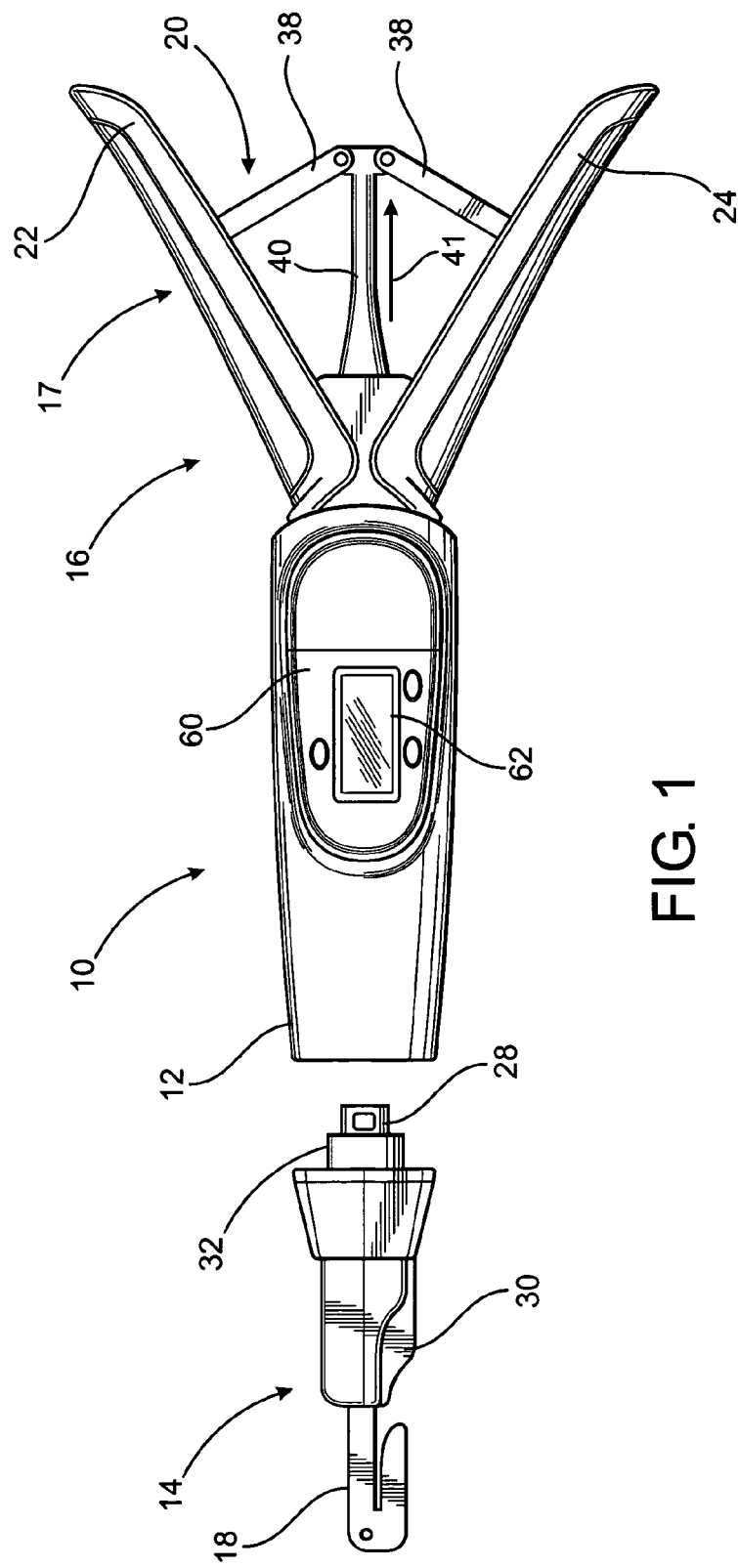
FIG. 1 is a perspective view of one preferred embodiment of the hair measuring assembly of the present invention.
Figure 2:
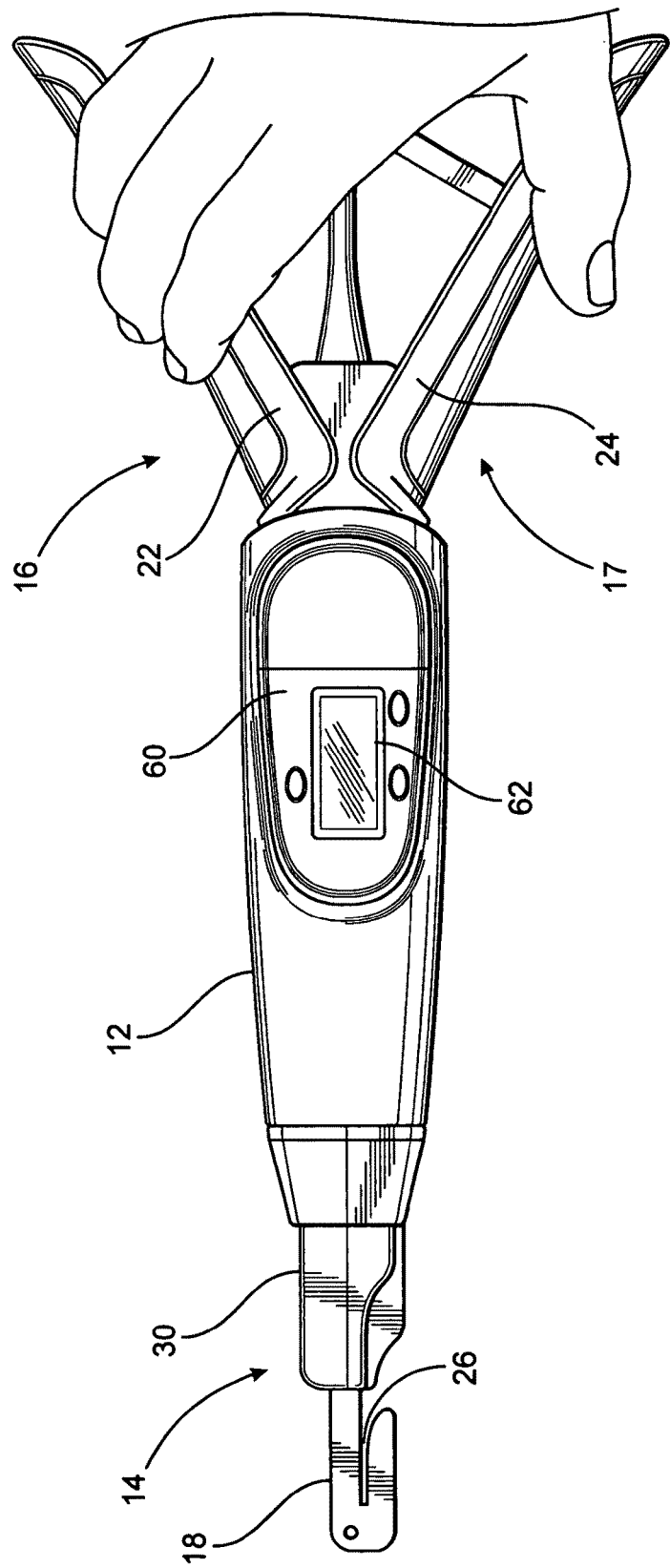
FIG. 2 is a perspective view of the embodiment of FIG. 1 in an assembled form.
Figure 3:
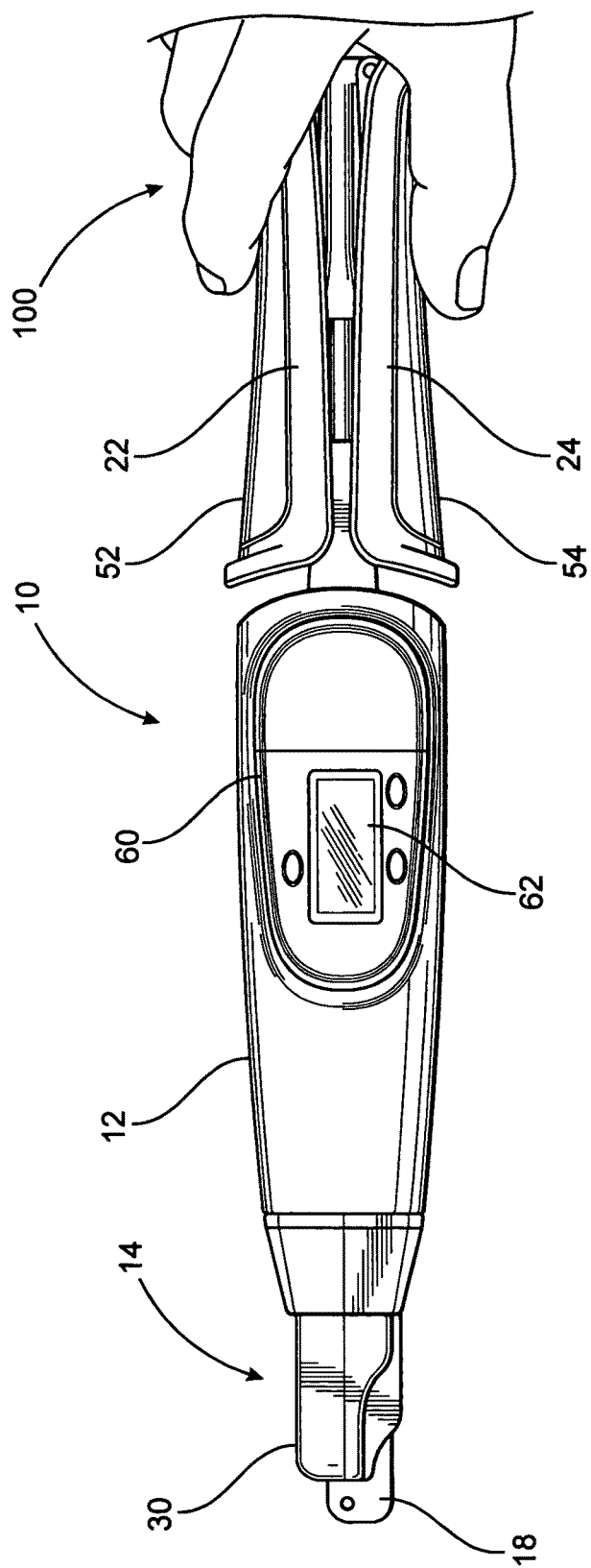
FIG. 3 is a perspective view of the embodiment of FIGS. 1 and 2 in a different operative position.

As represented in the accompanying drawings, the present invention is directed to an improved hair measuring assembly, which is generally indicated as 10. The assembly 10 includes an elongated body 12 having a hair collection assembly, generally indicated as 14, connected to one end thereof. An activation assembly, generally indicated as 16, is pivotally connected to the body 10 and selectively movable by a single hand of the user between an open orientation, as represented in FIGS. 1 and 2, and a closed orientation, as represented in FIG. 3. The open and closed orientations of the activation assembly includes a hand grip 17, which serves to selectively dispose the collection assembly 14, and more specifically, a hair retaining and measuring portion 18 associated therewith, between a hair collecting position, as best represented in FIG. 2, through an intermediate hair retaining position and into a hair retaining and measuring position, as best represented in FIG. 3.

Figure 4:
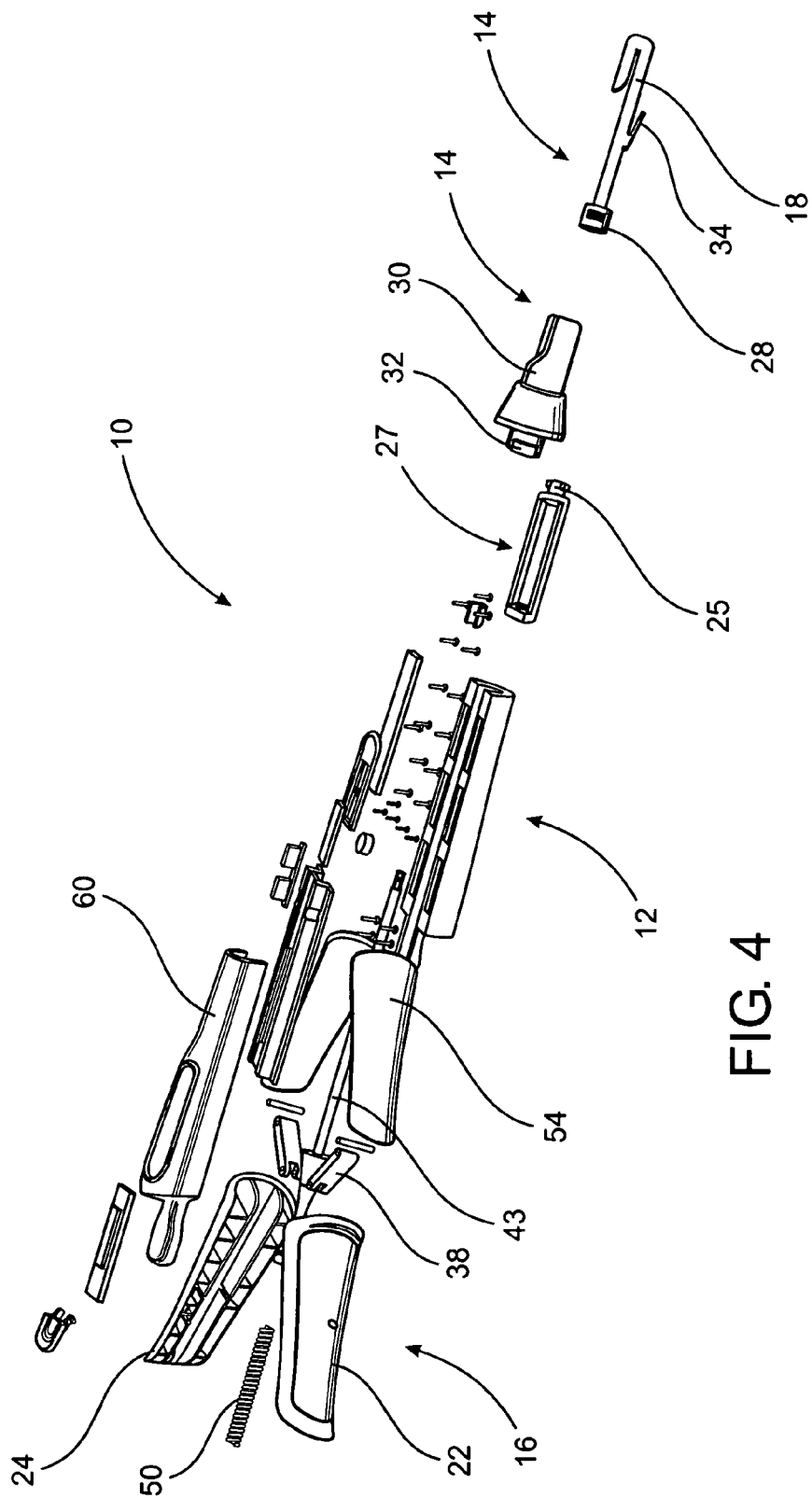
FIG. 4 is a perspective view in exploded form of the various components comprising the preferred embodiment of FIGS. 1 through 3.
Figure 6:
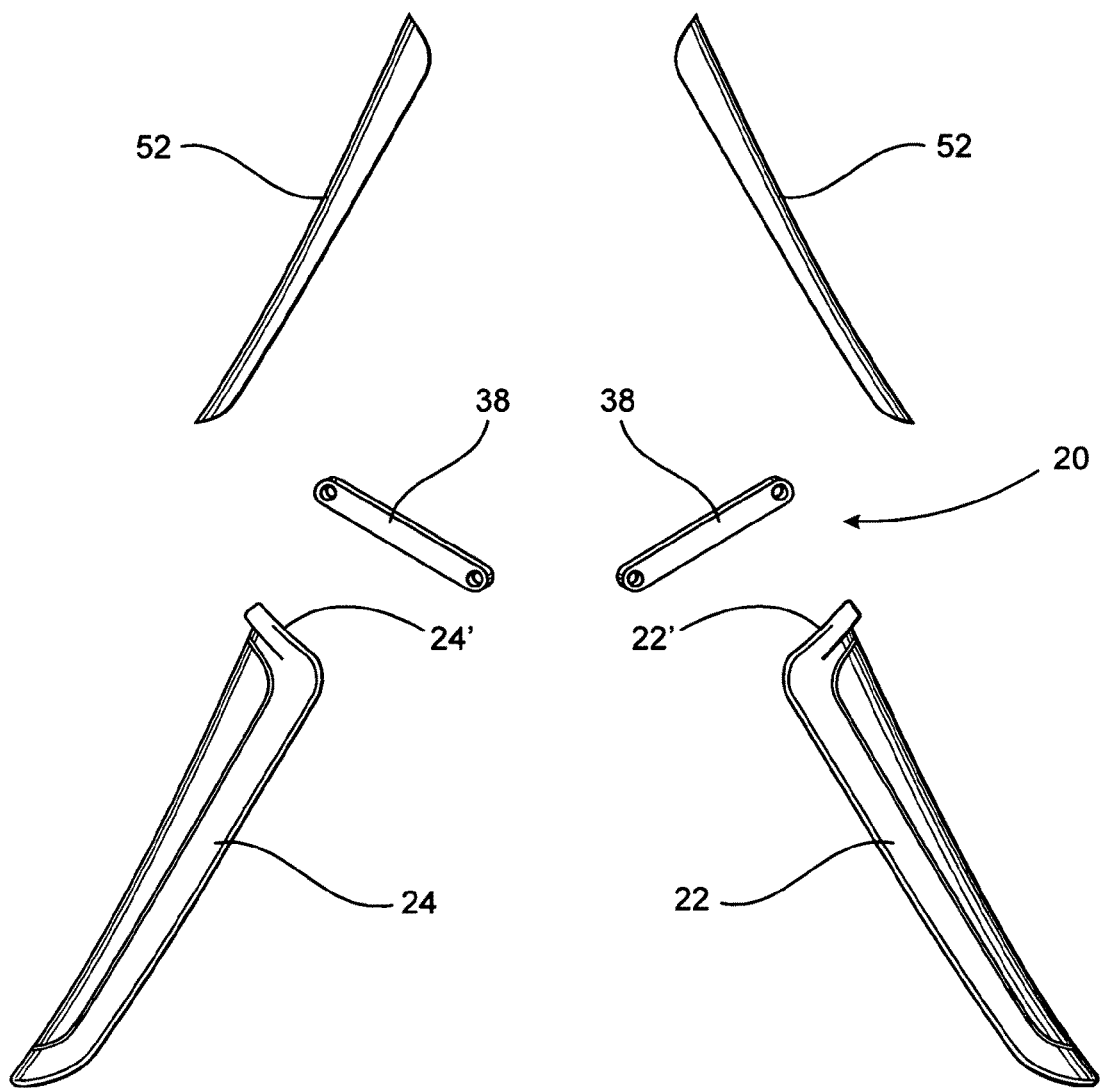
FIG. 6 is a perspective view in exploded form of the various components comprising an activation assembly of the embodiment of FIGS. 1 through 4.
Figure 7:
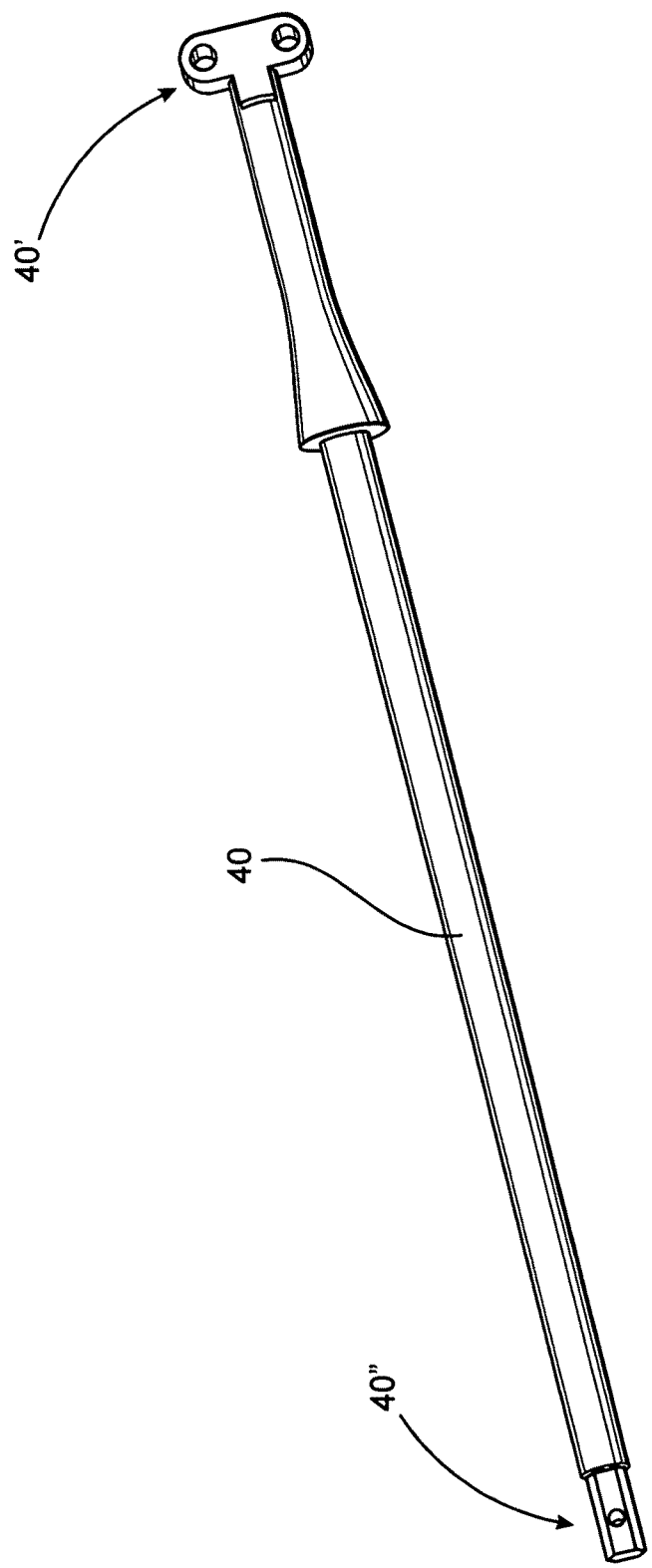
FIG. 7 is perspective view of a portion of a linkage assembly associated with the preferred embodiment of FIGS. 1 through 4.
Figure 8:
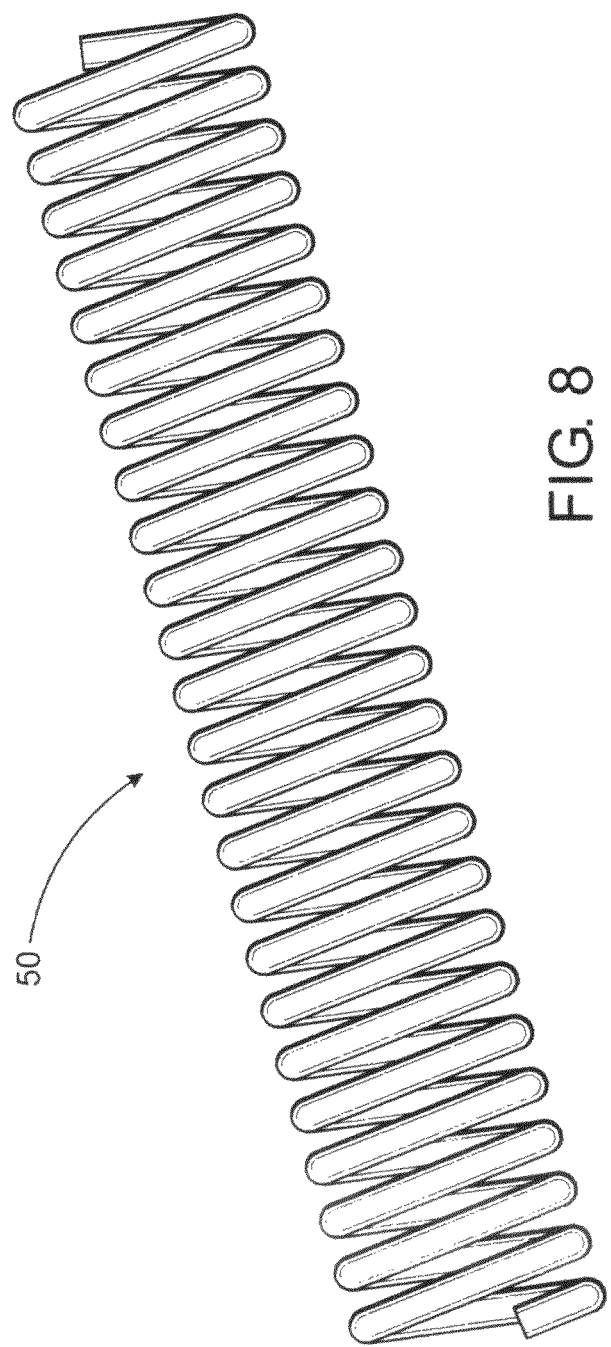
FIG. 8 is a biasing member associated with the structural and operative features of the embodiment of FIGS. 1 through 4.

In addition to the above, the activation assembly 16 further includes a linkage assembly, generally indicated as 20, and represented in more detail in FIGS. 4, 6 and 7. The activation assembly 16 may be more specifically defined as including at least one, but preferably, a plurality of two grip segments 22 and 24. Each of the grip segments 22 and 24 are pivotally connected at one end 22' and 24' respectively to the body 12, as represented. In addition, the structure, dimension and disposition of the two grip segments 22 and 24 are such as to facilitate their concurrent gripping and lateral, pivotal displacement relative to the body 12 between the open orientation, as represented in FIGS. 1 and 2 and the closed orientation, as represented in FIG. 3. As such, the open orientation may be accurately defined as the two grip segments and 24 being disposed in a laterally outward extending relation to the body 12, and in an angular orientation relative thereto, as clearly represented in FIGS. 1 and 2. In contrast, the closed orientation of the hand grip 17 may be accurately defined by the two grip segments 22 and 24 being disposed in a substantially longitudinal alignment with the body 12 and in substantially parallel or at least aligned relation to one another, as represented in FIG. 3. It is again emphasized that a single hand of the user, as at 100, may be used to selectively dispose the hand grip 17 between the open orientation of FIGS. 1 and 2 and the closed orientation of FIG. 3. This single handed operation allows the opposite or free hand of the user to hold, position or otherwise appropriately manipulate the hair being measured, such as to facilitate its positioning within the hair retaining and measuring portion 18, while it is disposed in the aforementioned collecting position.

Figure 5:
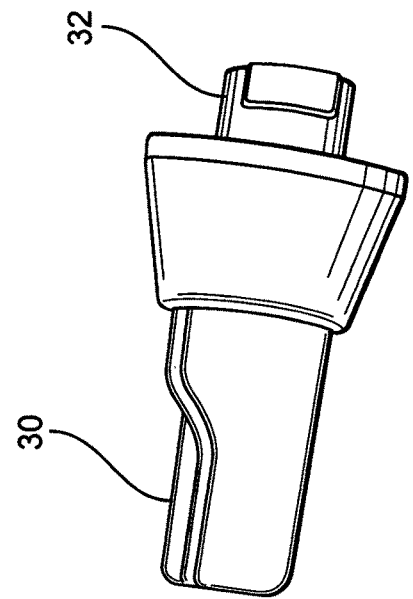
FIG. 5 is a detailed view in partially exploded form of a collection assembly of the embodiment of FIGS. 1 through 4.
Figure 5:
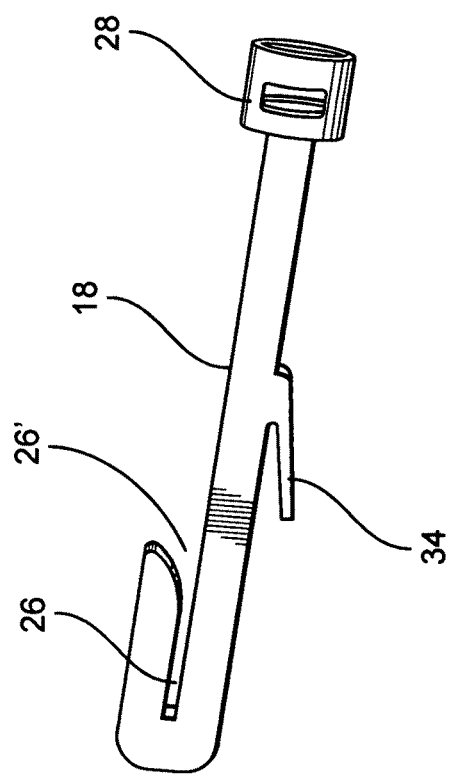

With primary reference to FIG. 5, the specific structural features of the collection assembly 14 are represented. As such, the hair retaining and measuring portion 18 will preferably include an elongated or other appropriate configuration which defines an open space or area 26, in which the hair being measured may be effectively collected. In doing so, the hair passes through an opening or access portion 26' possibly aided by the free hand of the user. The hair retaining and measuring portion 18 also includes a coupling 28 which in at least one embodiment may be structured to accomplish a removable connection with the aforementioned linkage assembly 20, as will be explained in greater detail hereinafter.

The collection assembly 14 further includes a housing or covering 30 structured to movably receive the hair retaining and measuring portion 18 therein, as represented in FIGS. 1 through 3. The housing 30 also includes a connection or coupling 32 which may be structured to accomplish a removable connection with the corresponding end of the body 12, as indicated in FIG. 1. Therefore, it should be apparent that the hair retaining and measuring portion 18, and most probably, the housing or covering 30 may be collectively disposed in a removable connection with the outer end or other corresponding portion of the body 12. More specifically, the hair retaining and measuring portion 18 includes a coupling 28 which may be detachably connected to a corresponding outer end 25 of a slider structure 27, as described in greater detail hereinafter. Similarly, the housing or covering 30 includes a coupling 32 which facilitates its detachable connection to the corresponding outer end of the body 12. This movable feature facilitates the replacement of the collection assembly 14, thereby allowing its commercial presentation as a single-use device. As such, repeated use of the collection assembly 14 and specifically the hair retaining and measuring portion 18 is prevented when repeated hair measurements are desired or required.

In order to further facilitate the "single use" application of the collection assembly 14, a locking member or assembly 34 may be connected at appropriate locations on the hair retaining and measuring portion 18. In at least one preferred embodiment, the locking member 34 represents a leaf spring construction formed of a sufficiently flexible material to allow a passage or retraction of at least part of the hair retaining and measuring portion 18 and the locking member 34 into the interior of the housing 30, and towards the body 12. When so positioned, the outward extension or positioning of the hair retaining and measuring portion 18 back into the hair collecting and retaining position will be prevented or restricted at least while the locking member or assembly 34 is engaged, due primarily to an abutting engagement of the end of the locking member 34 with one or more interior portions of the housing or covering 30.

Therefore, after a single use, the hair retaining and measuring portion 18 will, in one embodiment, become inoperative for additional uses and require that the collection assembly 14, preferably including both the housing or covering 30 and the hair retaining and measuring portion 18, be removable from the corresponding end of the housing 12. Additional features may include the couplings 28 and 32 respectively associated with the hair retaining and measuring portion 18 and the housing or covering 30 having "twist-off" connection. Such a connection enables rotation of the hair retaining and measuring portion 18 and housing or covering 30 in either a clockwise or counter-clockwise direction in order that it be removed or released from the body 12.

More in particular, the housing 30 and/or hair retaining and measuring portion 18 of at least one embodiment is removably attachable to the hair measuring device 10 and/or body 12 in any one of a plurality of at least two different operative orientations, and in particular, without regard as to whether the user thereof is left-handed or right-handed. The various operative orientations of the hair retaining and measuring portion 18 and/or housing 30 are defined and distinguishable by the direction in which the open area 26 of the hair retaining and measuring portion 18 is pointed or otherwise accessible relative to the remaining portions of the hair measuring device 10 and/or body 12 thereof. For exemplary purposes only, a left-handed user may be able to most effectively and efficiently use the device 10 with the open area 26 of the hair retaining and measuring portion 18 pointed in one direction relative to the body 12 and/or the visual display 62, whereas a right-handed user may be able to most effectively and efficiently use the device 10 with the open area 26 pointed in an opposite facing direction relative to the body 12 and/or visual display 62. Accordingly, the hair retaining and measuring portion 18 and/or housing is disposed in a removable and/or attachable relation to the body 12 in any of a plurality of operative orientations such that the direction or orientation of the open area 26 is at least partially adjustable according to a user's preference and to allow effective and efficient use of the device 10 by a left-handed and/or right-handed user. In at least one embodiment, the hair retaining and measuring portion 18 and/or housing 30 is disposed in a coupling relation to one another wherein a clockwise twisting motion will serve to attach the hair retaining and measuring portion 18 and housing 30 in one operative orientation, whereas a counter-clockwise twisting motion will serve to attach the hair retaining and measuring portion 18 and housing 30 in another different operative orientation.

As set forth above, the activation assembly 16 includes both the hand grip 17 as well as the linkage assembly 20. With primary reference to FIGS. 6 and 7, the linkage assembly 20 includes a first linkage structure 37 comprising at least one but preferably a plurality of two elongated link members 38 each being disposed to pivotally interconnect different ones of the grip segments 22 and 24 to a second linkage structure 40 represented in detail in FIG. 7. The second linkage structure 40 includes an elongated rod having one end, as at 40'', structured to be pivotally connected to corresponding ends of each of the elongated links 38 of the first linkage structure 37. As represented, each of the elongated links 38 include opposite end portions which are cooperatively structured with the connecting end 40' of the elongated rod or second linkage structure 40 to accomplish a pivotal interconnection there between and between the different ones of the grip segments 22 and 24.

Further, the opposite or outer end 40'' of the second linkage structure or rod 40 is structured to be removably interconnected to the hair retaining and measuring portion 18. More specifically, a length of the rod 40 disposed adjacent to the end 40'' passes through the interior slider 27, wherein the end 40'' connects to an end member 57 disposed in a sliding relation on the interior of the slider 27. In that the slider 27, and in particular the end 25 thereof, is removably connected to the coupling 28, as set forth above, the rod 40 can be accurately described as being removably interconnected to the hair retaining and measuring portion 18.

Moreover, the linkage assembly 20 comprises the first linkage structure including elongated links 38 disposed and structured to pivotally interconnect different ones of the grip segments 22 and 24 to the second linkage structure 40. In turn, the opposite or outer end 40'' of the second linkage structure or rod 40 is interconnected to the hair retaining and measuring portion 18 by means of the slider structure 27, as by detachable connection between ends 25 and coupling 28.

Therefore, it should be apparent that a single hand 100 of the user may concurrently and pivotally engage and dispose each of the grip segments 22 and 24 between the open orientation of FIGS. 1 and 2 into the closed orientation of FIG. 3. Therefore, when the hand grip 17 is in the open orientation, the hair retaining and measuring portion 18 extends linearly outward from the cover or housing a greater distance from the body 12 to assume the aforementioned collecting position, as best represented in FIG. 2. Once the hair being measured is disposed within the space or area 26, the single hand 100 of the user may concurrently exert a compressive force on both the handle segments 22 and 24, thereby pivotally displacing the handle segments 22 and 24 inwardly, into the closed orientation represented in FIG. 3.

When the grip segments 22 and 24 are in the closed orientation of FIG. 3, the second linkage structure 40 moves outwardly from the body 12, as indicated by directional arrow 41, thereby serving to retract the hair retaining and measuring portion 18 into the hair retaining and measuring position represented in FIG. 3. The hair retaining and measuring position is further defined by the hair retaining and measuring portion 18 being in close proximity to the cover or housing 30 as well as the body 12. As such, the housing or cover 30 is cooperatively disposed, dimensioned and structured with the hair retaining and measuring portion 18 to exert at an appropriate compressive force on the hair collected within the open space or area 26, in order that an accurate measurement may be obtained.

Other structural features associated with the hair measuring assembly 10 include a biasing member, generally indicated as 50. The biasing member 50 may be in the form of a coil spring or a variety of other biasing structures disposed in biasing relation to the second linkage structure 40. As a result, the rod or second linkage structure 40 has a biasing force exerted thereon which normally disposes the hair retaining and measuring portion 18, interconnected to the rod 40, in the aforementioned hair collecting position. Concurrently, the hand grip 17 and plurality of two grip segments 22 and 24 are disposed the open orientation as represented in FIGS. 1 and 2. The placement and structure of the biasing member 50 may vary, while its preferred placement may be disposed on the interior of the body 12 in biasing relation to the second linkage structure 40 and/or the hand grip 17, as set forth above. In addition to the above, an additional biasing structure, not shown for purposes of clarity, may be provided in the form of a coil spring or other configuration mounted on the interior of the body 12. This additional biasing structure may be appropriately disposed in biasing relation to the linkage assembly and/or the retaining portion so as to exert at an appropriate compressive force on the hair collected within the open space or area 26 of the hair retaining and measuring portion 18, in order that an accurate measurement of the collected hair may be obtained. Yet additional structural features may include outer surface inserts 52 removably or fixedly disposed in at least partially covering relation to corresponding ones of the grip segments 22 and 24. As such, the placement and overall structuring of the outer surface inserts 52 and 54 are such as to facilitate a gripping of the grip segments 22 and 24 by a single hand 100 of a user in a manner which avoids or reduces the possibility of slippage or discomfort.

Figure 9:
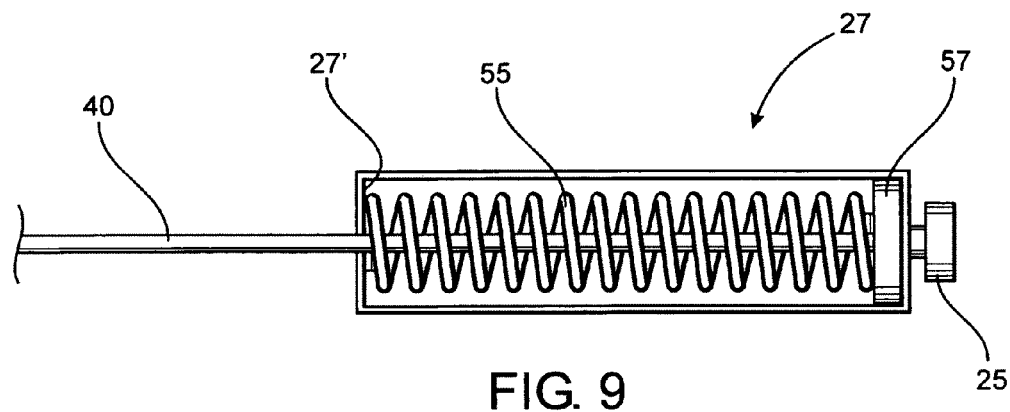
FIGS. 9 through 11 are schematic representations of the slider as disclosed in accordance with at least one embodiment of the present invention.
Figure 10:
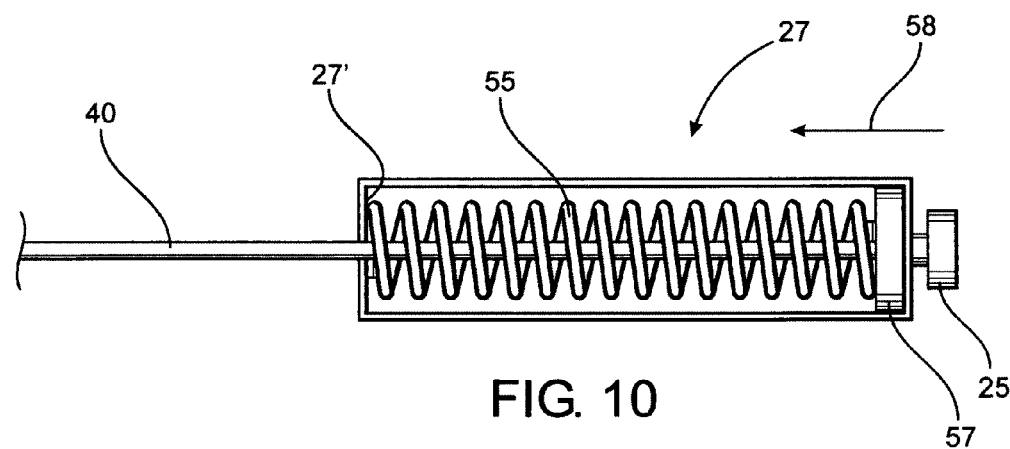
Figure 11:
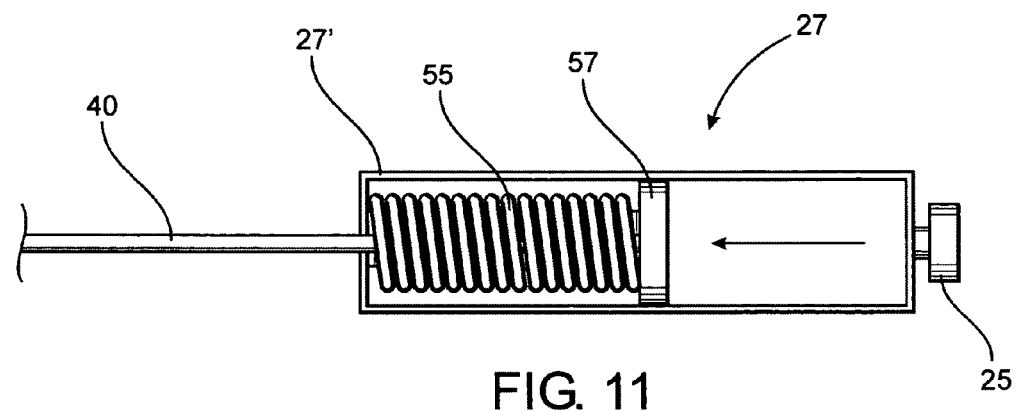

Furthermore, as best illustrated in FIGS. 9-11, other structural and operative features of the present invention includes a biasing member 55 disposed on the interior of the slider 27, and in particular, between a first interior end 27' and a movable end member 57. The biasing member 55 may be in the form of a coil spring or a variety of any other biasing structures or devices disposed in a biasing relation between the first end 27' and the end member 57. As a result, when the hair measuring assembly 10 is disposed in a relaxed or non-measuring state, for instance, when the activating assembly 16 is disposed in the open orientation, and/or the hair retaining and measuring portion 18 is extended linearly outward from the housing 30 to assume the collecting position (as shown in FIGS. 1 and 2), the biasing member 55 is structured to bias or otherwise exert a force on the end member 57 so as to dispose the end member 57 in an extended and/or relaxed orientation, as generally shown in FIG. 9. Once a collection of hair is disposed within the hair retaining and measuring portion 18, as discussed herein, the hair retaining and measuring portion 18 may be disposed from first hair collecting position, to a second or intermediate hair retaining position, and into a third hair retaining and measuring position. For instance, rod 40, end member 57 and slider 27 are structured to be movably disposed inward as a unit toward the activating assembly 16 (not shown in FIGS. 9-11), thereby disposing the hair retaining and measuring portion 18 at least partially within the housing or covering 30.

With minimal force manually applied to the activation assembly 16, thereby at least partially compressing the grip members 22, 24 toward one another, the bundle of hair is at least partially engaged or pinched within the hair retaining and measuring portion 18 while the hair retaining and measuring portion 18 is disposed in the second or intermediate hair retaining position. FIG. 10 generally illustrates the position of the slider 27 while the hair retaining and measuring portion 18 is disposed in the second hair retaining position. Specifically, the slider 27 and rod 40 are at least partially displaced inward toward the activation assembly 16, as illustrated by directional arrow 58. The biasing member 55, by the nature of its structure and compression or biasing strength, may, in at least one embodiment, be slightly compressed, and end member 57 may also slightly slide or move inward within slider 27, also in the direction indicated by arrow 58.

Finally, in order to position the hair retaining and measuring portion 18 into the third hair retaining and measuring position, such that the activating assembly 16 is disposed in the closed orientation (as illustrated in FIG. 3), an additional force is applied to the activation assembly 16 thereby disposing the biasing member 55 in an at least partially and further compressed or hair measuring orientation within the slider 27, as generally shown in FIG. 11. The amount of additional pressure needed to dispose the biasing member 55 into the compressed or hair measuring orientation is dependant upon the particular biasing member 55 and the relative biasing characteristics and strengths thereof.

Again with primary reference to FIGS. 1 through 3, the hair measuring assembly 10 of the present invention also includes a display assembly, generally indicated as 60, which is cooperatively disposed and structured with the linkage assembly 20, or other components disposed and structured to provide an indication of the displacement or position of the hair retaining and measuring portion 18 and/or the rod 40 when the hair to be measured is collected within the interior 26 of the hair retaining and measuring portion 18 when the retaining portion is disposed in the hair retaining and measuring position. The display assembly 60 includes a visual display as at 62 which represents indicia indicative of the dimensional characteristics of the hair being measured. The display assembly 60 may be electronically operated and as such as may be powered by an appropriate battery assembly.

In addition, at least one embodiment of the present invention further comprises a calibration key 70 cooperatively structured to calibrate the device 10 for use with a removable, replaceable, and/or "single-use" hair retaining and measuring portion 18 or cartridge. For instance, the calibration key 70 comprises a blade member 72 cooperatively structured and dimensioned to correspond to and be disposable within the open area 26 of the hair retaining and measuring portion 18. Moreover, the blade member 72 comprises a predetermined longitudinal dimension or length L. The length L of the blade member 72 is either pre-programmed into the internal electronic components of the device 10 or a user may selectively identify or input the length L into the internal electronic components of the device 10.

As can be understood, the precise dimensions, thickness, or tolerances of one "single use" and/or removable hair retaining and measuring portion 18 or cartridge may be at least slightly different than the precise dimensions, thickness, or tolerances of another "single use" and/or removable hair retaining and measuring portion 18 or cartridge. The dimensional differences may be due to certain manufacturing variances as well as other possible causes. In light of this, it is preferable to calibrate the device 10 prior to each use so that the device 10 and/or the internal electronic components are compatible or precisely adjusted to accommodate the varying dimensions of the removable cartridges.

In order to do so, the calibration key 70, and in particular, the blade member 72 thereof, is disposed within the open area 26 of the hair retaining and measuring portion 18. The hair retaining and measuring portion 18 is then movably disposed toward the housing 30 and into a calibrating position, for instance via disposition of the activation assembly 16 toward the closed orientation. The calibrating position of the hair retaining and measuring portions 18 is defined as a position wherein the blade member 72 is engaged within the open area 26 such as by the hair retaining and measuring portion 18 on one end and the housing 30 on the other end. Because the blade member 72 comprises a predetermined longitudinal length L, the device 10, and in particular, the internal electronic measuring components thereof, may be calibrated while the hair retaining and measuring portion 18 is disposed in the calibrating position. For exemplary purposes only, the blade member 72 of the calibration key 70 may comprise a predetermined longitudinal length L of four millimeters (4 mm). While the hair retaining and measuring portion 18 is disposed in the calibrating orientation, and thus while the blade member 72 is engaged within the open area 26, the internal electronic measuring components and programming thereof may be calibrated or "zeroed" so as to train or teach the device 10 of the specific dimensions of the hair retaining and measuring portion 18 and/or housing 30, which, as above, may vary depending on a number of factors including manufacturing variances. Once the device 10 is calibrated, the removable, "single-use" cartridge may be used to precisely measure hair, as discussed herein.

Figure 12:
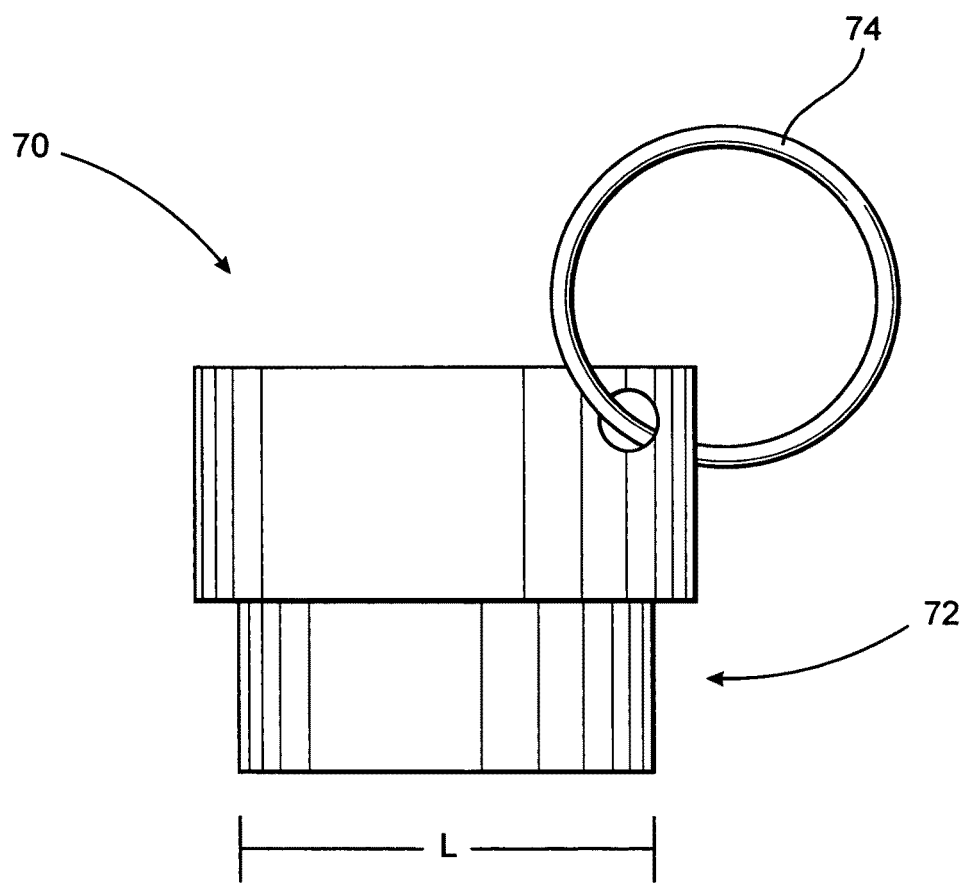
FIG. 12 is a schematic representation of a calibration key in accordance with at least one embodiment of the improved hair measuring assembly of the present invention.

Furthermore, as illustrated in FIG. 12, the calibration key 70 of at least one embodiment comprises a storage or retention member 74 which may be in the form of a ring as illustrated, one or more clips, hooks, loops, etc. When the device 10 is not in use, the storage member 74 of the calibration key 70 may be disposed in a storing or engaging relation with a portion of the device 10. For instance, the storage member or ring 74 may be disposed in a surrounding and retaining relation with the activation assembly 16, at least while the activation assembly 16 is disposed in the closed orientation. Accordingly, the activation assembly 16, and in particular, the grip segments 22, 24 may be disposed in the closed orientation and/or disposed in a substantially parallel relation to one another such that the ring 74 is disposable in a surrounding and retaining relation thereto.

The present invention further comprises a method of measuring a cross-section of hair using and implementing the device 10 described and disclosed herein. In practicing the method, a portion or bundle of a patient's or user's hair is isolated using any one of a number of strategies, including the use of a comb or brush which may also be used in combination with a marking template. A cartridge, including a hair retaining and measuring portion 18 and a housing 30, is attached to the body 12 of the device 10, as discussed above. Again, the cartridge may be disposed or attached to the body 12 in any of a number of operative orientations so as to suit the particular user, who may be either left-handed or right-handed.

Once the cartridge is attached to the device 10, the calibration key 70 may be used to "calibrate" the device 10, and in particular, the internal electronic measuring components thereof. As discussed above, the hair retaining and measuring portion 18 is disposed in a calibrating position wherein the calibration key 70 is disposed and engaged within the open area 26. Using certain controls located on the exterior of the body 12, a user may "zero" out the device 10 so as to "calibrate" and train the internal electronic measuring components to be associated with or adjusted to the precise dimensions of the removable cartridge.

The bundle of hair may then be measured by the device 10 as discussed above. In particular, the hair is placed within the open area 26 and the hair retaining and measuring portion is passed from the collecting position through an intermediate hair retaining position and into a hair retaining and measuring position. The displacement of the hair retaining and measuring portion 18, as adjusted in terms of the calibration, if necessary, is used to determine the precise measurement of the bundle of hair.

It should be appreciated that the "single use" aspect of the invention may be accomplished by or with the locking assembly 34. That is, the locking assembly 34 is structured to prevent the hair retaining and measuring portion 18 from returning to the collecting position once it has been disposed into the hair retaining and measuring position. However, once disposed in the hair retaining and measuring position, the locking assembly 34 of at least one embodiment is structured to allow the hair retaining and measuring portion 18 to be disposed in another "released" or "sliding" position, wherein the bundle of hair disposed or measured therein is capable of being released or removed, for instance via a sliding relation, from within open area 26 the hair retaining and measuring portion 18. The "released" or "sliding" position may be defined as a position between the hair retaining and measuring position and the collecting position allowing a user to remove the bundle of hair disposed therein, but restricting or otherwise making it difficult to dispose another bundle of hair within the hair retaining and measuring portion. It should be considered within the scope of the present invention to eliminate this feature.

For exemplary purposes, a section or bundle of hair may be measured from a zone or area on the user's scalp or head that is not experiencing hair loss or where hair loss is atypical, such as, for instance, at or near the bottom of the rear portion of the head. The results of this measurement may be compared to a measurement of a bundle of hair where the patient or user is experiencing hair loss or where hair loss is typical, such as, for instance, at the crown of the head or proximate the top portion of the head. The comparison may lead to results determinative of the individual's hair loss at or proximate the measured zones.

As another example, a portion or bundle of the individual's hair where hair loss is occurring, expected, or typical may be measured as discussed herein. Sometime later, for instance, two, three, or four weeks later, the same or substantially the same portion or bundle of hair may be measured and compared to the first or prior measurement(s) to determine or calculate the extent of the individual's hair loss.

As discussed above, at least one embodiment of the collection assembly 14 comprises a locking member or assembly 34 structured to prevent more than one single use of the cartridge or collection assembly 14. In light of this, each successive measurement of different bundles of hair on the same or different individuals must use a new cartridge or collection assembly 14. Thus, after the first measurement (such as at a location where hair loss is uncommon), the cartridge (hair retaining and measuring portion 18 and housing 30) is removed from the body 12, and a new cartridge is attached. Thereafter, the device 10 may then be calibrated to accommodate any possible dimensional variances in the new cartridge. Another measurement (such as at a location where hair loss is typical) may then be conducted.

In addition to measuring or determining hair loss, the device 10 of the various embodiments of the present invention may also be used to measure or determine the extent of an individual's hair breakage. For instance, once a bundle of hair is segregated for measurement, the device 10 may be used to measure the bundle of hair at a plurality of positions along the length thereof so as to measure or determine the extent of the individual's hair breakage, at least at the measured bundle site. The same "single use" cartridge as disclosed in accordance with at least one embodiment of the present invention may, but need not necessarily, be utilized to measure multiple areas of the same bundle of hair. In particular, the cartridge or collection assembly 14 may be used to measure the selected bundle of hair at a first position along the length thereof, for instance at or near the hair roots or proximate the individual's scalp. After the first measurement, the activation assembly 16 and/or grip member 22, 24 are released and the hair retaining and measurement portion is relaxed, at least until the locking assembly 34 is engaged, thereby preventing the hair retaining and measuring portion 18 from being disposed in the first collecting position. With the hair retaining and measuring portion 18 at least partially released from the measuring position, the device 10, and specifically, the hair retaining and measuring portion 18 may slide along the length of the bundle of hair to a second position where a subsequent measurement may be obtained without the need for replacing the cartridge or collection assembly 14. In this regard, a plurality of measurements of the same or substantially the same bundle of hair may be taken using the above described slidable relation along the length of the bundle of hair using the same collection assembly 14. Of course, however, a new cartridge or collection assembly 14 may be used for each measurement along the length of the bundle of hair if desired.

The internal electronic measurement components of the device 10 are structured to obtain and store the various measurements along the length of the same bundle of hair and based upon the results obtained, automatically calculate the extent of the individual's hair breakage. For example, a user may select "Hair Breakage Index," "HBI," or an equivalent selection on the device 10 in order to set the device 10 and the internal electronic measurement components to a hair breakage mode. Once in the hair breakage mode, the device 10 is structured to obtain and store the successive measurement results along the length of the bundle of hair, and based thereon calculate the extent of the individual's hair breakage.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A hair retaining and measuring assembly comprising:
   a body,
   a single-use collection assembly disposed in a removable relation to said body, said single-use collection assembly comprising a hair retaining and measuring portion and a housing,
   at least a part of said hair retaining and measuring portion movable within said housing and relative to said body, said hair retaining and measuring portion being disposable between a collecting position and a hair retaining and measuring position,
   an activating assembly movably mounted on said body and structured to selectively dispose said hair retaining and measuring portion between said collecting position and said hair retaining and measuring position,
   said activating assembly including a hand grip and a linkage assembly,
   said hand grip comprising two grip segments each movably connected to said body in spaced relation to one another, said two grip segments concurrently disposed, by a single hand of a user, between an open orientation and a closed orientation, and
   a locking assembly including a locking member mounted on and movable with said hair retaining and measuring portion within said housing, said locking member structured to engage an interior portion of said housing and thereby prevent movement of said hair retaining and measuring portion back into said collecting position after movement of said hair retaining and measuring portion and said locking member into said hair retaining and measuring position.

2. An assembly as recited in claim 1 wherein said single-use collection assembly is selectively disposable into any of a plurality of operative orientations relative to said body.

3. An assembly as recited in claim 1 wherein said linkage assembly comprises at least a first linkage structure and a second linkage structure; said first linkage structure pivotally connecting said hand grip to said second linkage structure, and said second linkage structure movably interconnecting said hair retaining and measuring portion to said first linkage structure.

4. An assembly as recited in claim 3 wherein said linkage assembly and said two hand grip segments are cooperatively structured to dispose said hair retaining and measuring portion in said collecting position when said two grip segments are in said open orientation, and further dispose said hair retaining and measuring portion in said hair retaining and measuring position when said two grip segments are disposed in said closed orientation.

5. An assembly as recited in claim 4 wherein said closed orientation comprises said two grip segments disposed in substantially longitudinally aligned relation with said body.

6. An assembly as recited in claim 5 wherein said open position comprises each of said two grip segments disposed laterally outward from said body and in an angular orientation relative thereto.

7. An assembly as recited in claim 6 wherein said two grip segments are cooperatively disposed and dimensioned for concurrent engagement and pivotal displacement, by the single hand of the user, from said open orientation towards said body and into said closed orientation.

8. An assembly as recited in claim 7 wherein said hair retaining and measuring position is at least partially defined by disposition of said hair retaining and measuring portion in sufficiently close proximity to a remainder of said body to facilitate compression of the hair being measured within said hair retaining and measuring portion.

9. An assembly as recited in claim 8 further comprising a display assembly connected to said body and structured to present indicia representative of dimensional characteristics of the hair being measured.

10. An assembly as recited in claim 1 further comprising a calibration key disposable in an engaging relation within an open receiving area of said hair retaining and measuring portion, at least while said hair retaining and measuring portion is disposed in a calibrating position.

11. An assembly as recited in claim 10 wherein said calibrating position is at least partially defined as said hand grip being at least partially compressed by the single hand of the user while said calibration key is disposed within said open receiving area of said hair retaining and measuring portion.

12. A hair measuring assembly comprising:
a body,
a collection assembly removably attached to said body and comprising a hair retaining and measuring portion structured to contain hair being measured therein,
said hair retaining and measuring portion movably connected to said body and disposed between a collecting position and a measuring position,
an activating assembly movably mounted on said body and structured to selectively dispose said hair retaining and measuring portion from said collecting position into said measuring position,
said activating assembly comprising a hand grip pivotally connected to said body and a linkage assembly,
said hand grip comprising at least two grip segments each concurrently and movably disposed between an open orientation and a closed orientation,
said linkage assembly pivotally interconnected between said hand grip and said collection assembly and movable with said hand grip to selectively dispose said hair retaining and measuring portion from said collecting position into said measuring position, and
a locking member mounted on said hair retaining and measuring portion and movable therewith in said housing; said locking member disposed and structured to engage an interior portion of said housing and thereby prevent movement of said hair restraining and measuring portion from said measuring position into said collecting position.

13. An assembly as recited in claim 12 wherein said linkage assembly comprises at least a first linkage structure and a second linkage structure, said first linkage structure pivotally connecting said hand grip to said second linkage structure and said second linkage structure movably interconnecting said hair retaining and measuring portion to said first linkage structure.

14. An assembly as recited in claim 12 wherein said two grip segments of said hand grip are each pivotally connected to said body in spaced relation to one another, said two grip segments are concurrently disposed, by a single hand of a user, between said open orientation and said closed orientation.

15. An assembly as recited in claim 14 wherein said closed orientation comprises said two grip segments disposed in longitudinally aligned relation with said body.

16. An assembly as recited in claim 15 wherein said closed orientation is further defined by said two grip segments disposed in parallel relation to one another.

17. An assembly as recited in claim 16 wherein said open orientation comprises each of said two grip segments disposed laterally outward from and in an angular orientation relative to said body.

18. An assembly as recited in claim 15 wherein said open orientation comprises each of said two grip segments disposed laterally outward from and in an angular orientation relative to said body.

19. An assembly as recited in claim 18 wherein said linkage assembly comprises at least a first linkage structure and a second linkage structure; said first linkage structure pivotally connecting said two grip segments to said second linkage structure and said second linkage structure movably interconnecting said hair retaining and measuring portion to said first linkage structure.

20. An assembly as recited in claim 19 wherein said first linkage structure comprises two elongated link members each movably interconnected to a different one of said two grip segments and said second linkage structure.

21. An assembly as recited in claim 20 wherein said first linkage structure comprises two elongated link members each pivotally connected to said second linkage structure and a different one of said two grip segments.

22. An assembly as recited in claim 12 further comprising a calibration key disposable within an open receiving area of said hair retaining and measuring portion.

23. An assembly as recited in claim 22 wherein said calibration key is disposed in an at least temporarily engaged relation within said open receiving area.

24. An assembly as recited in claim 23 wherein said calibration key comprises a blade member disposed in an engaged relation within said open receiving area of said hair retaining and measuring portion; said blade member comprising a predetermined longitudinal length.

25. An assembly as recited in claim 24 wherein said hair retaining and measuring portion is disposed between said collecting position and a calibrating position; said calibrating position comprising said blade member being disposed in said engaged relation within said open receiving area.

26. A method of measuring the hair breakage of a selected bundle of hair, comprising:
isolating the selected bundle of hair from a portion of a scalp,
attaching a single-use, removable collection assembly to a body of a hair measuring assembly, the single-use, removable collection assembly comprising a hair retaining and measuring portion and a housing, the hair retaining and measuring portion being disposable between a collecting position, a calibrating position, a measuring position, and a sliding position,
calibrating the hair measuring assembly by disposing a calibration key within an open receiving area of the hair retaining and measuring portion and disposing the hair retaining and measuring portion from the collecting position and into the calibrating position,
disposing the selected bundle of hair within the open receiving area of the hair retaining and measuring portion while the hair retaining and measuring portion is disposed in the collecting position,
engaging and measuring a first portion of the selected bundle of hair by disposing the hair retaining and measuring portion from the collecting position to the measuring position,
at least partially releasing the selected bundle of hair from an engaging relation with the hair retaining and measuring portion by disposing the hair retaining and measuring portion from the measuring position into the sliding position, the sliding position comprising a locking member mounted on and movable with the hair retaining and measuring portion within the housing into an engaging relation with an interior portion of the housing and thereby preventing the hair retaining and measuring portion from being disposed back into the collecting position after movement of the hair retaining and measuring portion at least temporarily into the measuring position, sliding the hair retaining and measuring portion along a length of the selected bundle of hair to a second portion of the selected bundle of hair and measuring the second portion by disposing the hair retaining and measuring portion from the sliding position to the measuring position.

* * * * *